United States Patent
Gordley et al.

(10) Patent No.: US 8,289,518 B2
(45) Date of Patent: Oct. 16, 2012

(54) GAS FILTER CORRELATION RADIOMETRY METHOD AND SYSTEM USING A DISSIMILAR GAS TO DETECT A TARGET GAS

(75) Inventors: Larry L Gordley, Grafton, VA (US);
Benjamin T Marshall, Williamsburg, VA (US)

(73) Assignee: G&A Technical Software Inc., Newport News, VA (US)

( * ) Notice: Subject to any disclaimer, the term of this patent is extended or adjusted under 35 U.S.C. 154(b) by 0 days.

(21) Appl. No.: 12/931,075

(22) Filed: Jan. 24, 2011

(65) Prior Publication Data

US 2012/0188548 A1    Jul. 26, 2012

(51) Int. Cl.
*G01N 21/00* (2006.01)

(52) U.S. Cl. .................. 356/437; 356/432

(58) Field of Classification Search .......... 356/432–442, 356/444; 250/336.1, 338.1, 339.01, 339.05, 250/338.5

See application file for complete search history.

(56) References Cited

U.S. PATENT DOCUMENTS

| | | | |
|---|---|---|---|
| 6,756,592 B1 * | 6/2004 | Smith et al. | 250/338.5 |
| 7,423,756 B2 | 9/2008 | Gordley | |
| 7,460,235 B2 | 12/2008 | Gordley | |
| 7,847,945 B2 * | 12/2010 | Gordley | 356/437 |

* cited by examiner

*Primary Examiner* — Tri T Ton
(74) *Attorney, Agent, or Firm* — Peter J. Van Bergen

(57) ABSTRACT

A Gas Filter Correlation Radiometer (GFCR) system and methods of using same are provided. The system's GFCR instrument includes a gas cell. A gas in the gas cell has a chemical composition that is different than that of a target gas in an atmospheric region being examined by the GFCR instrument. The gas included in the gas cell also possesses light absorption features with a portion thereof being at least partially correlated with light absorption features of the target gas. Measurement viewing(s) made with the GFCR instrument provide for at least one positive correlation for the portion of the at least partially correlated features so that the GFCR instrument generates a signal indicative thereof used in a gas filter correlation radiometry application.

18 Claims, 9 Drawing Sheets

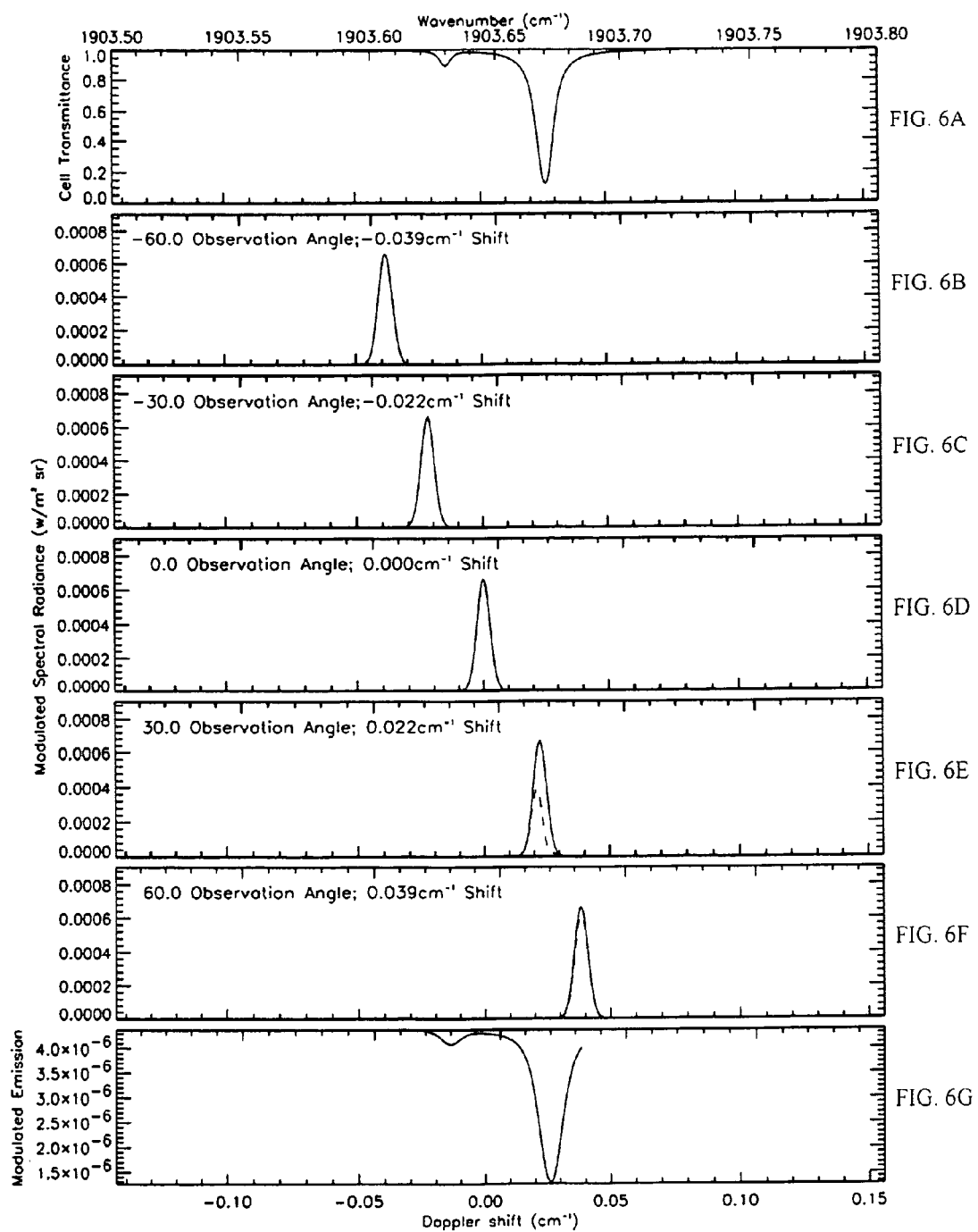

GAS FILTER CORRELATION RADIOMETRY METHOD AND SYSTEM USING A DISSIMILAR GAS TO DETECT A TARGET GAS

FIELD OF THE INVENTION

The invention relates generally to gas filter correlation radiometry, and more particularly to a gas filter correlation radiometry method and system that can detect/measure a target gas in an atmosphere using a gas having a chemical composition that is different than that of the target gas.

BACKGROUND OF THE INVENTION

Gas filter correlation radiometry is an optical remote sensing method used to produce highly sensitive measurements of a target gas present in an atmospheric region. In applying this method, a Gas Filter Correlation Radiometer (GFCR) instrument views a scene through a cell that includes a sample of the target gas to thereby create a high-resolution spectral "notch" filter. A "notch" filter is one that prevents the passage of light at narrow spectral locations as opposed to the typical filter that allows light to pass at one or more narrow spectral locations. The (target) gas in the cell will absorb light at exactly the spectral locations of the target gas absorption features to thereby create a filter that is almost perfectly correlated with the target gas. The target gas is detected by comparing measurements of total light over a limited spectral bandpass with and without the "notch" filter, or by comparing measurements with various "notch" filters (i.e., different gas concentrations in the gas cell of each "notch" filter). The former typically splits the beam creating multi-beams to make measurements, while the latter methods that compare signals by varying the "notch" filter typically use one beam and modulate the cell condition. Both measurement systems have a gas cell that includes a gas that is chemically identical to the target gas that is to be detected/measured.

Unfortunately, some target gases do not lend themselves to accurate detection and/or measurement using a GFCR instrument because the target gas's spectral absorption features are too weak or non-distinct to produce adequate absorption signatures in a gas cell environment and/or the target gas is chemically unstable in a gas cell environment. For example, detecting/measuring ozone with a GFCR instrument has been ineffective due to ozone's inherent instability that makes its containment in a GFCR system's gas cell problematic. In another example, the measurement of oxygen with a GFCR instrument is problematic because oxygen does not have sufficiently strong absorption features needed for a GFCR gas cell filter.

SUMMARY OF THE INVENTION

Accordingly it is an object of the present invention to provide a method and system for making gas filter correlation radiometry measurements of any target gas regardless of the target gas's suitability for use in a gas cell filter.

Another object of the present invention is to provide a method and system for making gas filter correlation radiometry measurements of target gases having absorption characteristics that are too weak to produce adequate absorptive filtering by a gas cell environment.

Still another object of the present invention is to provide a method and system for making gas filter correlation radiometry measurements of target gases that are chemically unstable in gas cell environments.

Other objects and advantages of the present invention will become more obvious hereinafter in the specification and drawings.

In accordance with the present invention, a Gas Filter Correlation Radiometer (GFCR) system and methods of using same are provided. The system has a GFCR instrument that includes a gas cell and a spectral filter that limits the spectral bandpass of the light entering the system. A measurement viewing is made by the GFCR instrument when light energy enters the system. Included in the gas cell is a gas having a chemical composition that is different than that of a target gas in an atmospheric region being examined by the GFCR instrument. The included gas possesses light absorption features with a portion thereof being at least partially correlated with light absorption features of the target gas. The measurement viewing is adjusted to generate at least one positive correlation for the portion of the at least partially correlated features so that the GFCR instrument generates a signal indicative thereof. A gas filter correlation radiometry application is performed using this signal.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 6A depicts a carbonic sulfide spectra for a gas cell;

FIGS. 6B-6F depict the measurement of a nitric oxide emission feature as viewed from orbit for unique observation angles when carbonic sulfide is the gas cell gas and nitric oxide is the target gas; and FIG. 6G depicts a GFCR signal that is an absorption feature shape as a function of shift using carbonic sulfide as the gas cell gas and nitric oxide as the target gas in accordance with another embodiment of the present invention.

DETAILED DESCRIPTION OF THE INVENTION

The present invention extends the utility of Gas Filter Correlation Radiometer (GFCR) instruments to the detection/measurement of virtually any atmospheric gas constituent regardless of the constituent's absorption characteristics and/or chemical stability in a GFCR instrument's gas cell environment. The approach described herein can be implemented in any GFCR instrument and method to include single-beam/single-detector instruments that are well known in the art, multi-beam/multi-element instruments such as those disclosed in U.S. Pat. Nos. 7,423,756 and 7,460,235, and GFCR instruments employing Doppler shifted measurements as disclosed in U.S. Pat. No. 7,847,945. Accordingly, it is to be understood that the term "GFCR instrument" as used herein generally includes the elements necessary to perform a gas filter correlation radiometry application.

Figure 1:
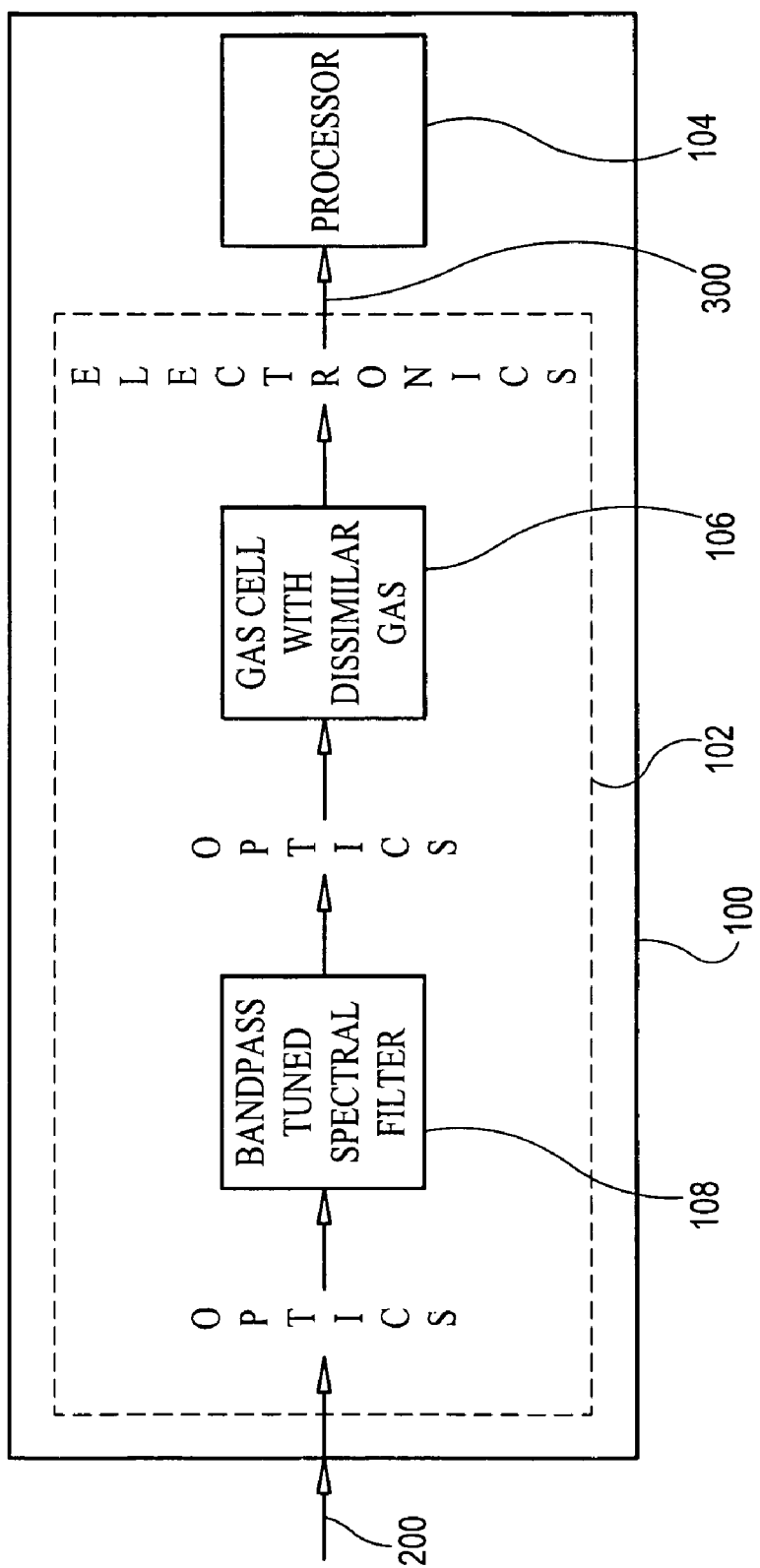
FIG. 1 is a schematic view of a GFCR instrument illustrating the novel aspects thereof in accordance with an embodiment of the present invention.

Referring now to the drawings and more particularly to FIG. 1, an embodiment of a GFCR instrument incorporating the novel features of the present invention is shown and is referenced generally by numeral 100. GFCR instrument 100 defines a processing "train" 102 for incoming light energy 200 impinging thereon. It is assumed that light energy 200 has passed through an atmospheric region of interest that includes some atmospheric target gas that is to be detected/measured.

As would be understood in the art, processing train 102 includes optical elements/systems (illustrated in FIG. 1 as "OPTICS") as well as electronic elements/systems to include detectors (illustrated in FIG. 1 as "ELECTRONICS") that cooperate to convert a measurement viewing of light 200 to a signal 300 that can be used by a processor 104 in the performance of a gas filter correlation radiometry application. The particular choices of elements/systems for the OPTICS and ELECTRONICS used in processing train 102 are not limitations of the present invention as they can be selected to satisfy the operational requirements of a particular application. In addition, it is to be understood that processing train 102 could be a single-beam or multiple-beam system without departing from the scope of the present invention. Processor 104 can be incorporated in GFCR instrument 100 or could be separated therefrom without departing from the scope of the present invention. The details of processing train 102 that are well known in prior art GFCR instruments have been omitted from FIG. 1 for sake of clarity. Such details can be found, for example, in the above-cited U.S. Pat. Nos. 7,423,756, 7,460,235, and 7,847,945, the contents of which are hereby incorporated by reference.

In accordance with the present invention, GFCR instrument 100 (i.e., a single-beam or multiple-beam GFCR instrument) includes a gas cell 106 and a bandpass-tuned spectral filter 108 in processing train 102. However, the details of gas cell 106 and spectral filter 108 depart from the teachings of prior art GFCR instruments and gas filter correlation radiometry measurement methods. The present invention includes a gas in gas cell 106 that is chemically dissimilar from the atmospheric target gas, but specifically used to induce a signal correlation with the atmospheric target gas that GFCR instrument 100 is attempting to detect/measure. That is, gas cell 106 need not include the atmospheric target gas as is the case in prior art GFCR instruments, and could even exclude the target gas in many applications. Instead, gas cell 106 includes a gas that merely shares one or more light absorption "feature locations" (i.e., wavenumber locations) with those of the atmospheric target gas. The number of correlated features with the atmospheric target gas is likely to be less than conventional GFCR instruments having gas cells populated with a sample of the target gas. Thus, the signal produced by the correlated features is more likely to be corrupted by spectral noise and anti-correlations.

GFCR instrument 100 must be adjusted to minimize signal corruption and/or anti-correlation effects in the present invention. Such adjustment can be accomplished in different ways depending on the particular application. In the illustrated example where gas cell 106 includes a gas that shares some light absorption features with the atmospheric target gas, adjustment is made by proper selection and/or tuning of spectral filter 108. Specifically, spectral filter 108 defines or is tuned to a bandpass where the absorption features shared by the atmospheric target gas and the dissimilar gas included in gas cell 106 are most strongly correlated. That is, spectral filter 108 limits the spectral range of light 200 seen by gas cell 106 to thereby limit the effects of spectral noise and anti-correlations. The correlations can be negative or positive, although positive correlations are more likely to be stronger thereby making their use more likely in the present invention. Spectral filter 108 can be realized by a variety of different methods to include use of interference filters, etalon filters, or combinations of interference and etalon filters. Thus, it is to be understood that the present invention is not limited by the type of spectral filter 108.

The (positive) correlations resulting at the output of gas cell 106 cause a signal 300 indicative thereof to be generated by the ELECTRONICS (to include detectors). Signal 300 is then further processed by, for example, processor 104 that can be programmed specifically for a gas filter correlation radiometry application, the choice of which is not a limitation of the present invention. Indeed, several embodiments of the present invention will be explained later herein.

Figure 2:
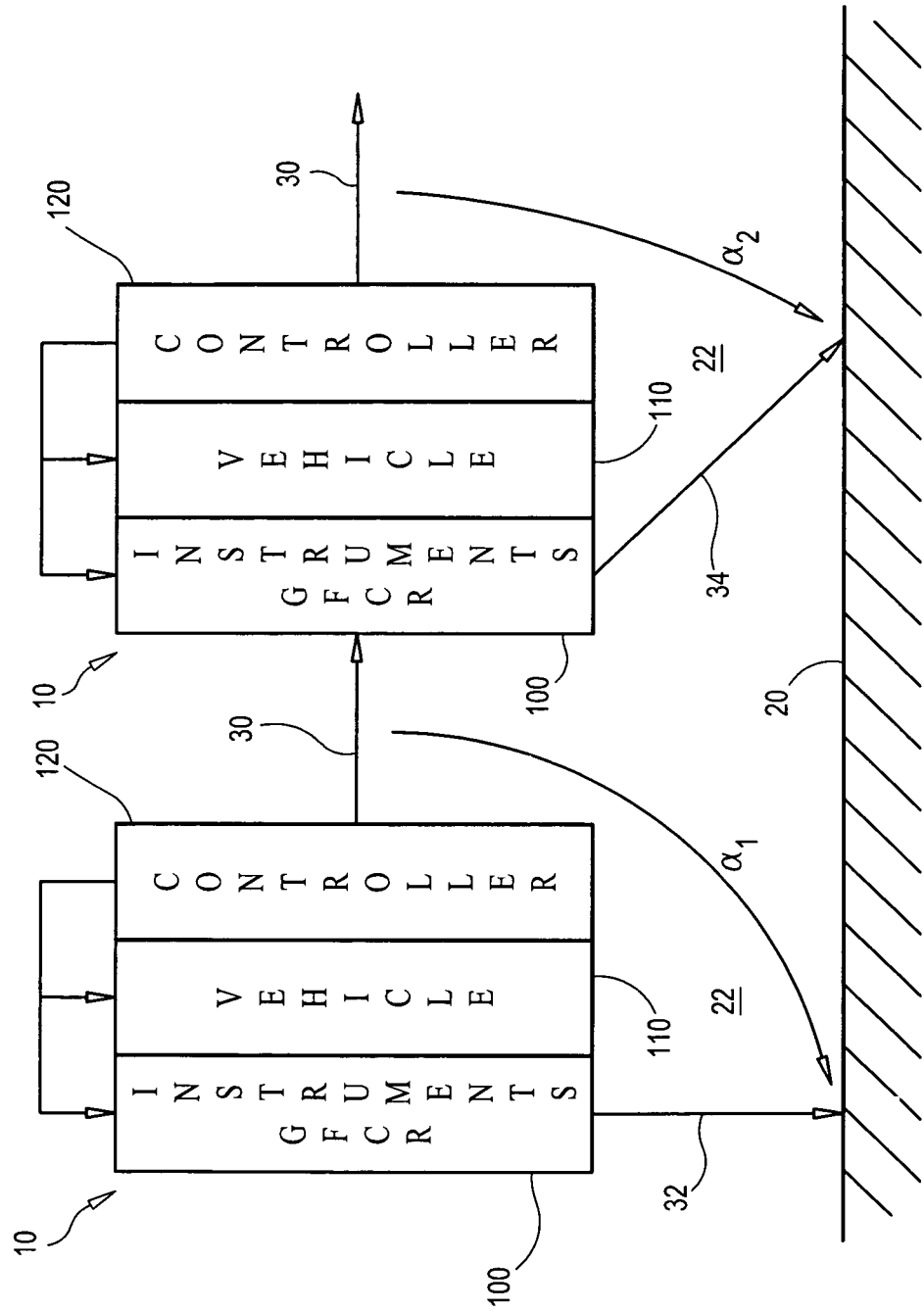
FIG. 2 is a schematic view of an orbiting GFCR system capable of viewing at various angles to produce Doppler shifted measurements in accordance with another embodiment of the present invention.

As mentioned above, the present invention applies to a variety of GFCR systems and methods to include those employing Doppler shifted measurement views as described in the previously-referenced U.S. Pat. No. 7,847,945. Accordingly, FIG. 2 illustrates a GFCR system 10 that can employ the teachings of the present invention in the Doppler shifted measurement approach. GFCR system 10 includes GFCR instrument 100 as described above. However, GFCR system 10 has the added advantage that the absorption features of the dissimilar gas included in the gas cell 106 (of GFCR instrument 100) need only be partially correlated with the absorption features of the atmospheric target gas. As used herein, the term "partially correlated" means that two feature peaks can be separated by several widths of the absorption feature. This increases the number of dissimilar gases that can be used in the present invention.

System 10 also includes a vehicle 110 coupled to GFCR instrument 100 for supporting and/or propelling GFCR instrument 100 in a spatial orbit about a heavenly body having a surrounding atmosphere such as the Earth, Mars, etc. The surface of the heavenly body is indicated by reference numeral 20 and the atmosphere thereof is referenced by numeral 22. Vehicle 110 could be a spacecraft, natural or man-made satellite, etc., that moves GFCR instrument 100 along a velocity vector referenced by numeral 30.

In GFCR system 10, GFCR instrument 100 is oriented to view a region of atmosphere 22 along a view direction. For example, in the illustrated embodiment, a view direction 32 is approximately perpendicular to both velocity vector 30 and surface 20. Solar light scattered from surface 20 (or thermal emission from surface 20 and/or atmosphere 22) is measured by GFCR instrument 100 as it "views" atmosphere 22 along view direction 32. As explained above, GFCR instrument 100 generates a signal indicative of the "view".

In accordance with the present invention, the measurement made along view direction 32 is taken when the relative velocity between GFCR instrument 100 and atmosphere 22 is zero or approximately zero. Light is also measured by GFCR instrument 100 while viewing atmosphere 22 along a second view direction 34 that is angularly displaced from view direction 32. That is, GFCR instrument 100 views atmosphere 22 along view direction 32 and generates a GFCR measurement signal indicative of atmospheric information in the view. After collecting the atmospheric data along view direction 32, GFCR instrument 100 is "pointed" to view atmosphere 22 along view direction 34 where another GFCR measurement signal is generated. The amount of time between such measurements and/or distance traveled by GFCR instrument 100 between such measurements are dependent on the gas filter correlation radiometry application that will use the measurements and are, therefore, not limitations of the present invention. Further, different view direction timing and strategies could be used. For example, different observations could be timed to allow observation of the same atmosphere at different angles.

In general, if view direction 32 forms an angle of $\alpha_1$ with velocity vector 30, view direction 34 forms an angle of $\alpha_2$ with velocity vector 30 where $\alpha_1$ is different than $\alpha_2$. It is to be understood that applications could use many observation angles without departing from the scope of the present invention. The amount of angular difference should be sufficient such that the atmospheric spectral features of atmosphere 22 associated with view direction 34 appear Doppler shifted with respect to the atmospheric spectral features of atmosphere 22 associated with view direction 32. The actual amount of angular difference will depend upon the gas filter correlation radiometry application using such measurements. In general, the view angles could be numerous and are typically defined relative to the zero velocity plane, which is approximately the plane perpendicular to the orbital velocity (relative to atmosphere) containing the observing instrument. Therefore, applications could include observations from nadir to limb (to include the upper atmosphere) of the heavenly body.

The present invention can implement the previously-described dissimilar gas measurement technique using observations (i.e., measurement views) of atmosphere 22 (to include any target gas of interest) under conditions of Doppler shift. When view direction 34 views a region of atmosphere 22 that is approaching GFCR instrument 100, the Doppler shift will cause the spectral features to stretch resulting in a wavelength dependent shift towards shorter wavelengths. Conversely, when view direction 34 views a region of atmosphere 22 that is moving away from GFCR instrument 100, the Doppler shift will cause the spectral features to contract resulting in a wavelength dependent shift towards longer wavelengths. Shifting in either direction will spectrally separate the gas cell spectral features relative to the corresponding atmospheric spectral features thereby inducing a change in the GFCR signal that can provide information for a host of analytical applications. Thus, the present invention is not limited to any set of observation angles used to induce Doppler shifts and change in correlated signal.

Combining the Doppler shifted measurement strategy with the dissimilar gas cell content approach of the present invention provides a number of observational advantages when performing various gas filter correlation radiometry processes or applications. For example, the Doppler shifting process can be used to "tune" GFCR system 10 so that the strongest absorption feature correlations can be found between the atmospheric target gas of interest and the dissimilar gas in the GFCR instrument's gas cell. Further, once the spectral limits producing the strongest correlations are identified, GFCR system 10 can be operated to modulate measurement views to produce spectral scans back and forth across the identified spectral limits. As a result, GFCR instrument 10 will produce a modulation signal that is highly correlated with the atmospheric target gas even if the absorption features of the dissimilar gas in the gas cell are only partially correlated with some absorption features of the atmospheric target gas.

To control the measurement views of GFCR instrument 100, GFCR system 10 can include a controller 120 that governs the view direction "seen" by GFCR instrument 100. Controller 120 could control physical manipulations of vehicle 110 and/or GFCR instrument 100 to change the measurement view direction thereof. However, controller 120 could also or alternatively control internal optics (not shown) of GFCR instrument 100 to achieve the various measurement view directions required for the Doppler shift approach to gas filter correlation radiometry measurements. Still another approach to achieve multiple measurement views is to image the atmosphere from orbit with an array detector (i.e., in the GFCR instrument's ELECTRONICS) that is large enough to observe signal change as the scene passes through the field-of-view of the image. More specifically, once controller 120 has positioned vehicle 110 and/or GFCR instrument 100 for a desired field-of-view, each point in the field-of-view incurs a different spectral shift as "seen" by the array detector. Thus, it is to be understood that a variety of methods can be used to produce different angles of observations without departing from the scope of the present invention.

The advantages of the present invention are numerous. Measurements made with GFCR instruments are no longer limited to those that can be accomplished with a target gas in the instrument's gas cell. Rather, any gas is now a candidate for use in detecting the target gas as long as that gas will produce stable spectral features in a gas cell while only needing some of those features to correlate or partially correlate with the target gas features.

The number of applications that could utilize the present invention is extensive. By way of non-limiting examples, four embodiments of the present invention will be described below. It is important to note that none of the four embodiments can be accomplished with prior art GFCR instruments/methods. Thus, the present invention is a major advancement in the field of GFCR instruments/methods.

Example 1

Illustrated in FIGS. 3A-3H

Measurement from an Earth orbit of ozone ($O_3$) near the Earth's surface using carbonic sulfide (OCS) in the GFCR instrument's gas cell.

Example 2

Illustrated in FIGS. 4A-4H

Measurement from an Earth orbit of atmospheric column density by measuring oxygen ($O_2$) absorption using hydrogen fluoride (HF) in the GFCR instrument's gas cell.

Example 3

Illustrated in FIGS. 5A-5H

Measurement from a Mars orbit of the column density of water vapor ($H_2O$) using methane ($CH_4$) in the GFCR instrument's gas cell.

Example 4

Illustrated in FIGS. 6A-6G

Measurement from an Earth orbit of the wind velocity along the observation direction by determining the spectral position of a nitric oxide (NO) emission line relative to the gas cell line feature using carbonic sulfide in the GFCR instrument's gas cell. The same measurement yields the spectral feature width to thereby also provide kinetic temperature over altitudes of the atmosphere at a sufficiently low pressure.

Each of the first three examples is illustrated by eight figures. The "A" figure shows a dissimilar gas cell spectra. The "B" through "F" figures illustrate both atmospheric transmission spectra of the atmosphere alone and the combination of the atmosphere and gas cell transmission as viewed from orbit for unique observation angles. In each of these figures, the solid-line curve results from the atmosphere alone and the dashed-line curve results from the atmosphere and the gas cell transmission. The different observation angles cause a different apparent shift of the atmospheric spectra. The "G" figure depicts the total integration transmission between the curves as a function of shift. Finally, the "H" figure illustrates the GFCR signal that would be generated as a function of shift. Specifics for the different embodiments will be explained below.

In general, the "H" figures show the GFCR signal as a function of view angles/shift spectra. The "H" figures illustrate that the GFCR signal at specific shifts is highly correlated with the target gas, and that combining that with a change in observation direction produces observed spectral shifts that create an even more distinct signal that is highly correlated with the target gas. All examples illustrate applications made possible by the combination of the present invention's dissimilar gas cell technique with the Doppler modulation technique described in U.S. Pat. No. 7,847,945. Shifting the observed atmospheric spectra makes it possible to effectively move the relative position of absorption features to produce correlated line positions and, therefore, strong GFCR signals.

Figures 3A, 3B, 3C, 3D, 3E, 3F, 3G:
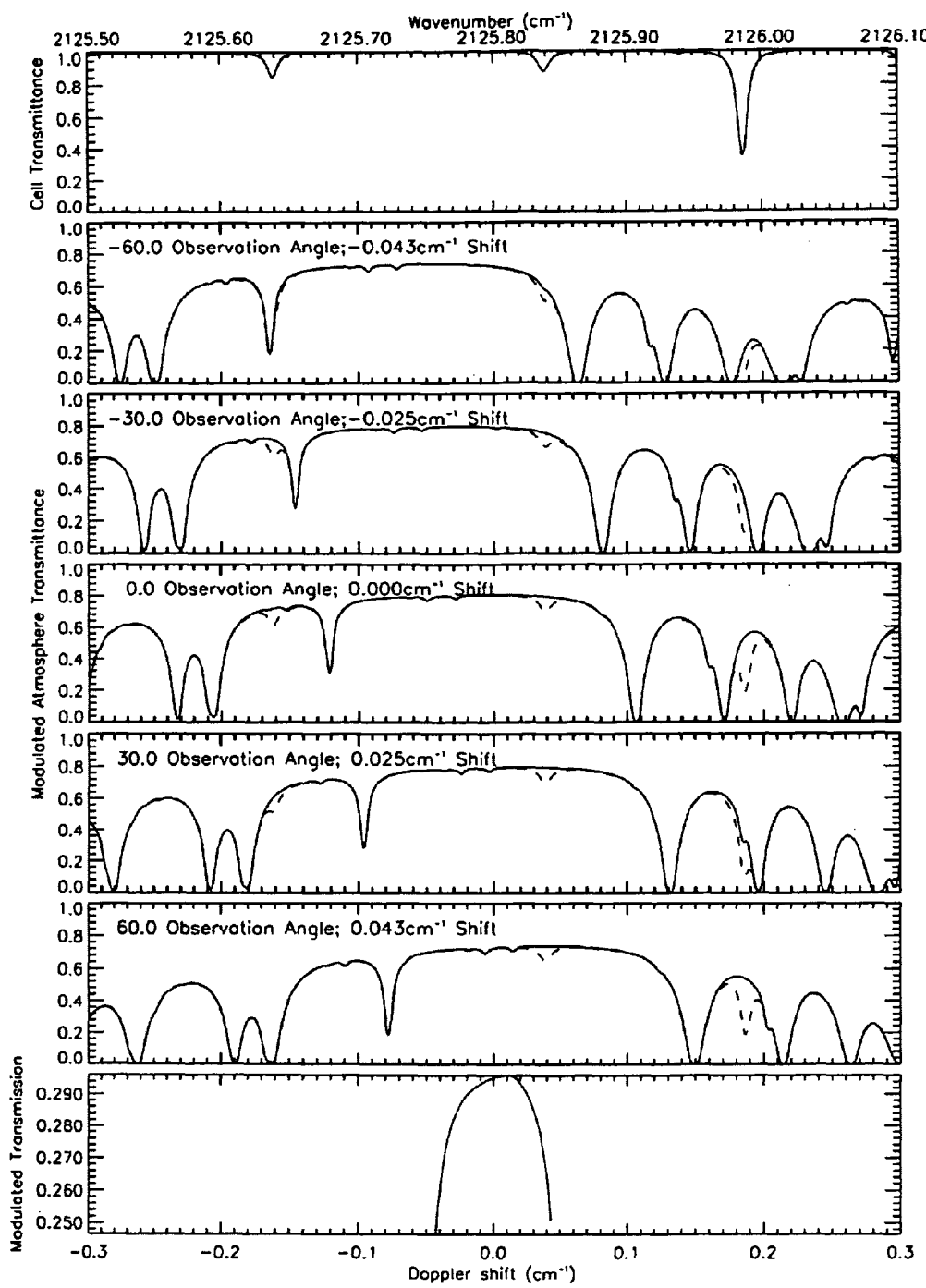
FIG. 3A depicts a carbonic sulfide spectra for a gas cell.
FIGS. 3B-3F depict the atmospheric transmission spectra of the atmosphere alone and the combination of the atmosphere and gas cell transmission as viewed from orbit for unique observation angles when carbonic sulfide is the gas cell gas and ozone is the target gas.
FIG. 3G depicts a total integrated transmission as a function of shift.
Figure 3H:
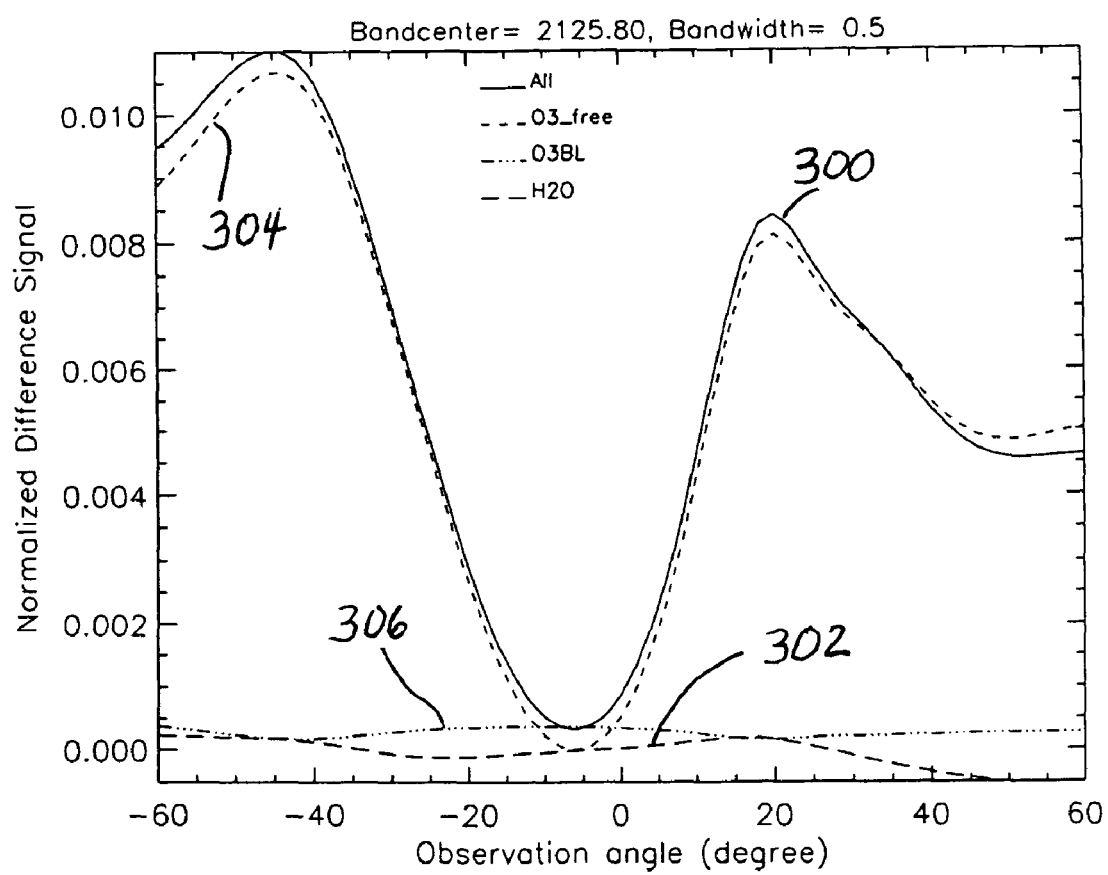
FIG. 3H depicts a GFCR signal that would be generated as a function of shift using carbonic sulfide as the gas cell gas and ozone as the target gas in accordance with an embodiment of the present invention.

In EXAMPLE 1, FIG. 3H illustrates the GFCR signal that would be generated as a function of shift. There are several curves in the plot. Solid curve 300 represents the signal resulting from all gasses in the atmosphere. Dashed-line curve 302 represents the signal resulting from just water. Dotted-line curve 304 represents the signal resulting from just ozone above 5 kilometers. Dashed-dotted curve 306 represents the signal resulting from just ozone below 5 kilometers (commonly referred to as boundary layer or "BL" ozone). Each point on solid curve 300 represents the GFCR signal at that shift or observation direction. The breakthrough capability provided by the present invention is a signal generated with an observation near −5 degrees off nadir that is nearly 100% due to BL ozone.

Figures 4A, 4B, 4C, 4D, 4E, 4F, 4G:
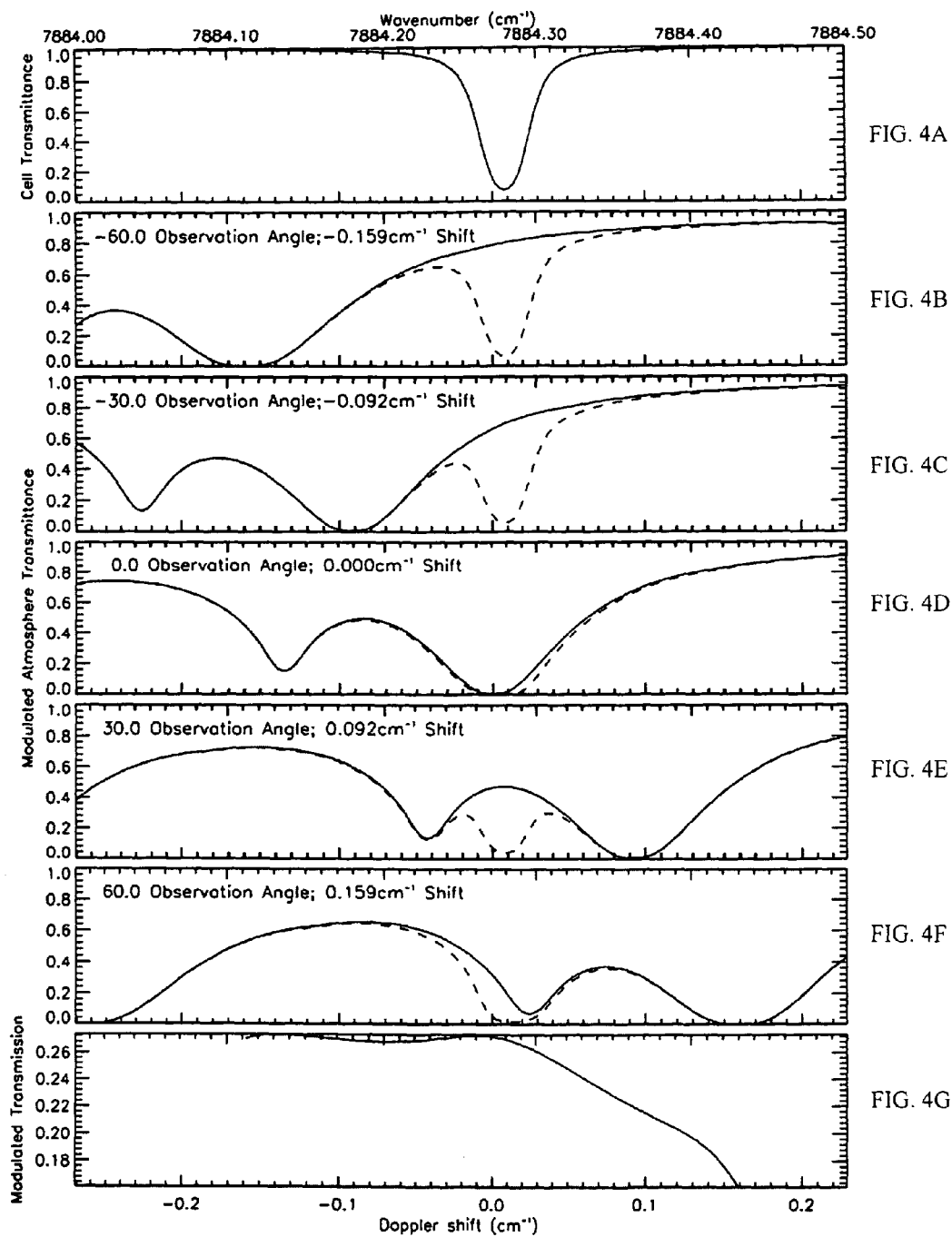
FIG. 4A depicts a hydrogen fluoride spectra for a gas cell.
FIGS. 4B-4F depict the atmospheric transmission spectra of the atmosphere alone and the combination of the atmosphere and gas cell transmission as viewed from orbit for unique observation angles when hydrogen fluoride is the gas cell gas and oxygen is the target gas.
FIG. 4G depicts a total integrated transmission as a function of shift.
Figure 4H:
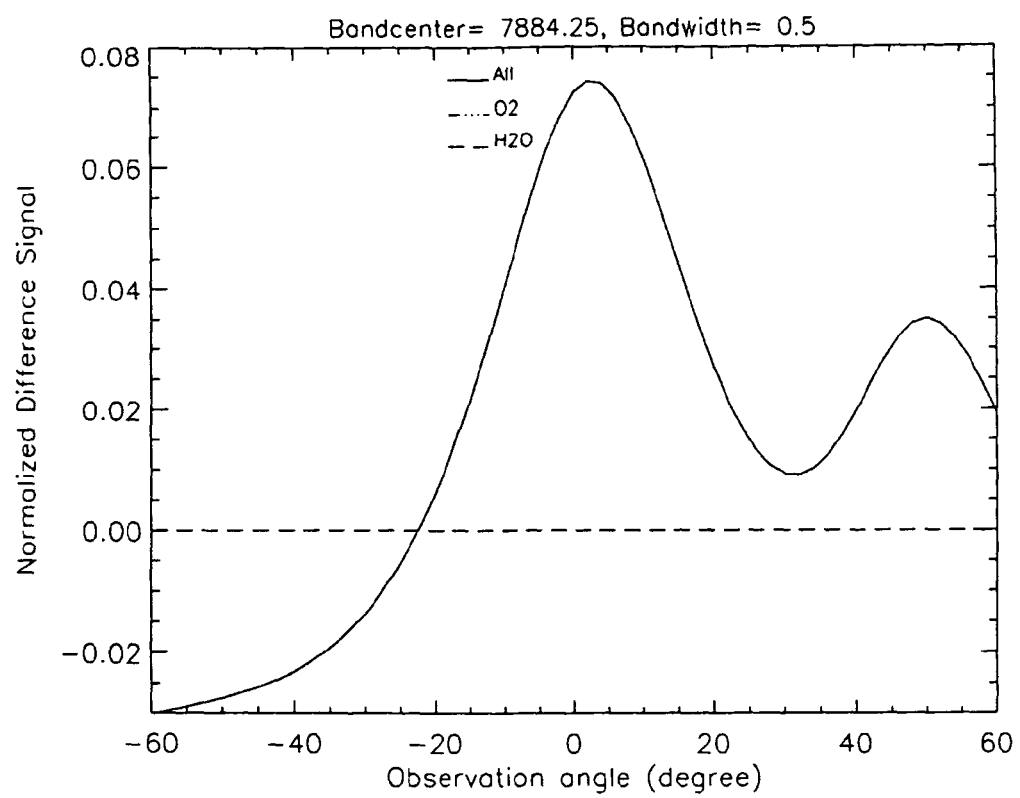
FIG. 4H depicts a GFCR signal that would be generated as a function of shift using hydrogen fluoride as the gas cell gas and oxygen as the target gas in accordance with another embodiment of the present invention.
Figures 5A, 5B, 5C, 5D, 5E, 5F, 5G:
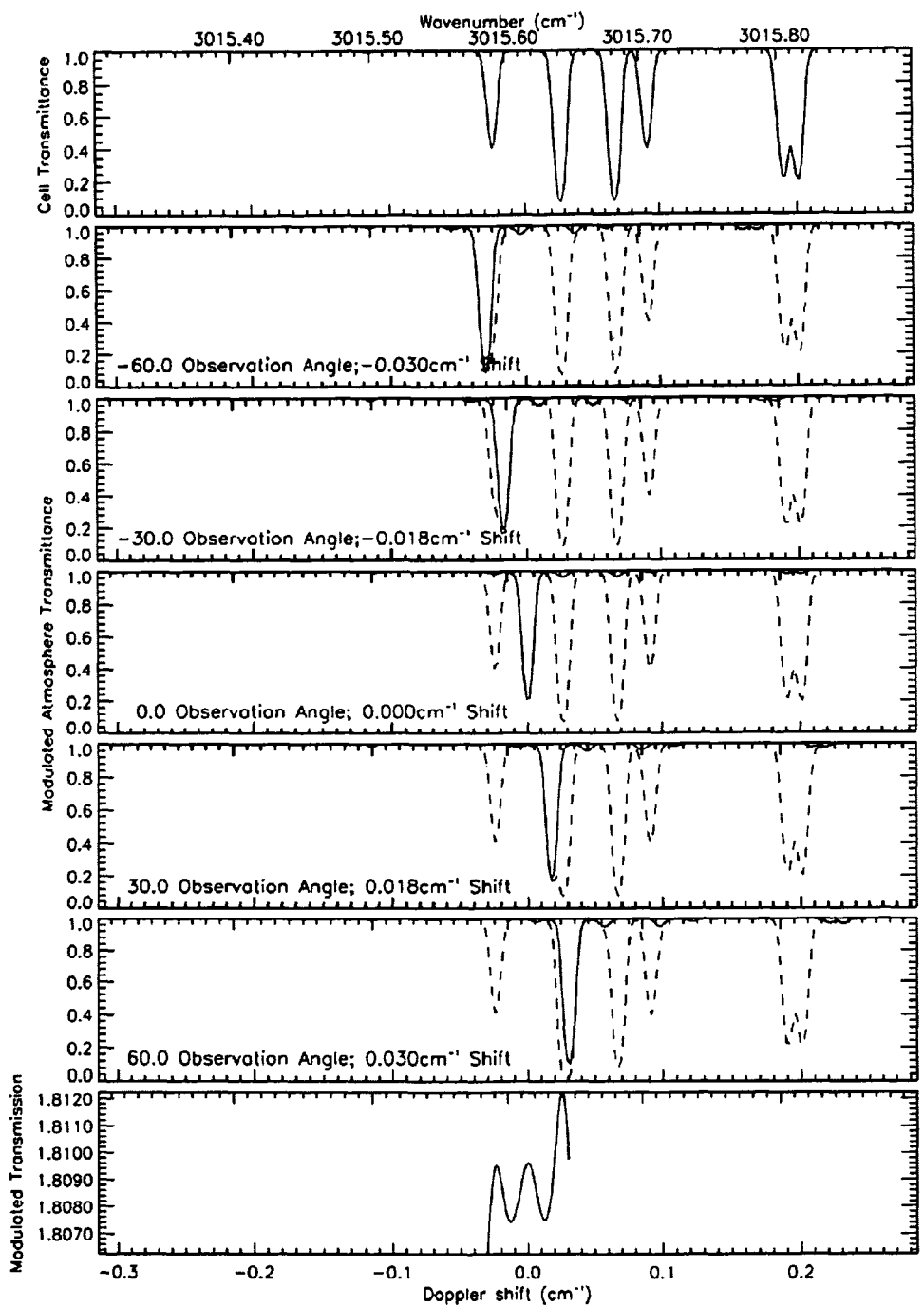
FIG. 5A depicts a methane spectra for a gas cell.
FIGS. 5B-5F depict the atmospheric transmission spectra of the atmosphere alone and the combination of the atmosphere and gas cell transmission as viewed from a Mars orbit for unique observation angles when methane is the gas cell gas and water vapor is the target gas.
FIG. 5G depicts a total integrated transmission as a function of shift.
Figure 5H:
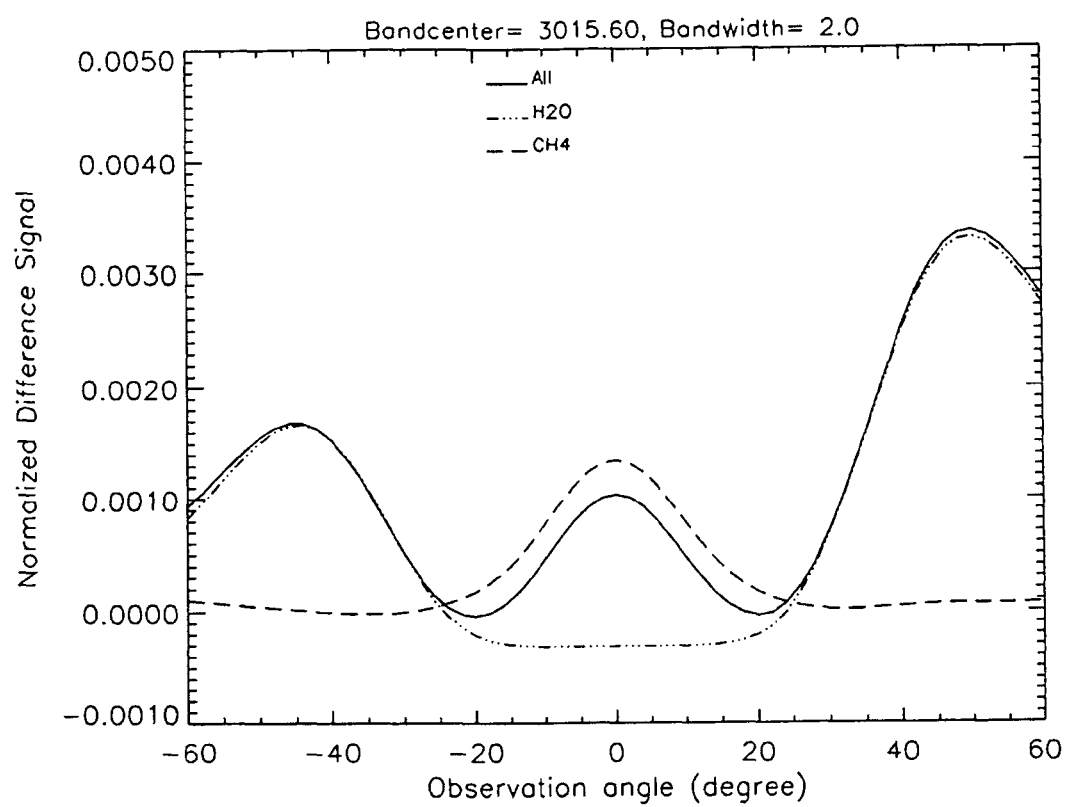
FIG. 5H depicts a GFCR signal that would be generated as a function of shift using methane as the gas cell gas and water vapor as the target gas in accordance with another embodiment of the present invention.

In EXAMPLE 2, FIG. 4H illustrates a high spectral resolution scan of nadir oxygen transmission spectra, which is known in the industry to produce not only determination of total air column abundance, but some altitude distribution information as well. No other passive technique can obtain this information with such spectral resolution.

In EXAMPLE 3, a strong methane line (FIG. 5A) creates a strong absorption feature in a gas cell that correlates with an observed atmospheric water line that is shifted over the methane line by observing in a direction that provides the proper Doppler shift. By scanning through these observation angles, a distinct and bias-insensitive signal (solid-line curve in FIG. 5H) is created that is highly correlated with water concentration. EXAMPLE 4 uses the same approach to effectively scan a carbonic sulfide gas cell feature (FIG. 6A) with a nitric oxide emission feature. The apparent spectral location of the resulting signal (FIG. 6G), in combination with known spacecraft motion and attitude, allows accurate estimate of wind velocity component along the observational vector, while the width of the signal shape as a function of shift provides a temperature measurement.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A gas filter correlation radiometry method, comprising the steps of:
   providing a Gas Filter Correlation Radiometer (GFCR) instrument capable of making a measurement viewing through a gas cell;
   selecting a gas that (i) is chemically dissimilar from a target gas of interest that is in an atmospheric region being examined by the GFCR instrument, and (ii) possesses light absorption features with a spectral portion of said light absorption features of said gas being at least partially correlated with light absorption features of the target gas of interest;
   populating the gas cell with said gas;
   adjusting said measurement viewing through said gas in the gas cell to generate at least one positive correlation for said spectral portion of said light absorption features of said as that is at least partially correlated with said light absorption features of the target gas of interest, wherein the GFCR instrument generates a signal indicative of said at least one positive correlation; and
   performing a gas filter correlation radiometry application for the target gas of interest using said signal so-generated from said at least one positive correlation.

2. A method according to claim 1, wherein said gas is selected from the group consisting of methane, carbonic sulfide, and hydrogen fluoride.

3. A method according to claim 1, wherein said gas filter correlation radiometry application comprises the measurement of column density of water vapor from a Mars orbit, and wherein said gas comprises methane.

4. A method according to claim 1, wherein said gas filter correlation radiometry application comprises the measurement of ozone in proximity to the Earth's surface, and wherein said gas comprises carbonic sulfide.

5. A method according to claim 1, wherein said gas filter correlation radiometry application comprises the measurement of wind velocity and atmospheric temperature from an Earth orbit using nitric oxide as the target gas of interest, and wherein said gas comprises carbonic sulfide.

6. A method according to claim 1, wherein said gas filter correlation radiometry application comprises the measurement of atmospheric column density from an Earth orbit using oxygen as the target gas of interest, and wherein said gas comprises hydrogen fluoride.

7. A method according to claim 1, wherein said step of adjusting includes the step of spectrally filtering said measurement viewing.

8. A method according to claim 1, wherein said step of adjusting includes the step of manipulating the GFCR instrument wherein said measurement viewing is scanned over said spectral portion.

9. A method according to claim 1, wherein said step of adjusting includes the step of modulating said measurement viewing back and forth over said spectral portion.

10. A Gas Filter Correlation Radiometer (GFCR) system, comprising:

a GFCR instrument that includes a gas cell and a spectral filter, wherein a measurement viewing is made by said GFCR instrument when light energy passes through said spectral filter and said gas cell;

a gas populating said gas cell, said gas (i) being chemically dissimilar from a target gas of interest that is in an atmospheric region being examined by said GFCR instrument, and (ii) possessing light absorption features with a spectral portion of said light absorption features of said gas being at least partially correlated with light absorption features of the target gas of interest; and said spectral filter defining a bandpass where positive correlations for said spectral portion can be generated, wherein said GFCR instrument generates a signal indicative of said positive correlations, and wherein said GFCR instrument performs a gas filter correlation radiometry application for the target gas of interest using said signal so-generated from said positive correlations.

11. A system as in claim 10, wherein said gas is selected from the group consisting of methane, carbonic sulfide, and hydrogen fluoride.

12. A system as in claim 10, wherein said gas comprises methane when the target gas of interest is water vapor.

13. A system as in claim 10, wherein said gas comprises carbonic sulfide when the target gas of interest is ozone.

14. A system as in claim 10, wherein said gas comprises hydrogen fluoride when the target gas of interest is oxygen.

15. A system as in claim 10, wherein said gas comprises carbonic sulfide when the target gas of interest is nitric oxide.

16. A system as in claim 10, wherein said spectral filter includes at least one of an interference filter and an etalon filter.

17. A system as in claim 10, further comprising means coupled to said GFCR instrument for scanning said measurement viewing over said spectral portion.

18. A system as in claim 10, further comprising means coupled to said GFCR instrument for modulating said measurement viewing back and forth over said spectral portion.

* * * * *